United States Patent [19]
Lee et al.

[11] Patent Number: 5,438,336
[45] Date of Patent: Aug. 1, 1995

[54] FOCAL PLANE IMAGING ARRAY WITH INTERNAL CALIBRATION SOURCE

[75] Inventors: Paul S. C. Lee, La Palma; Pei-Ming D. Chow, Los Angeles; John J. Berenz, San Pedro; Jay S. Pearlman, Rancho Palos Verdes; Wayne W. Lam, Manhattan Beach, all of Calif.

[73] Assignee: TRW Inc., Redondo Beach, Calif.

[21] Appl. No.: 151,713

[22] Filed: Nov. 12, 1993

[51] Int. Cl.$^6$ .................................................. G01S 7/40
[52] U.S. Cl. ........................................ 342/174; 342/53
[58] Field of Search ................ 342/25, 52, 53, 54, 342/66, 91, 92, 167, 174

[56] References Cited

U.S. PATENT DOCUMENTS

| | | | |
|---|---|---|---|
| 4,313,678 | 2/1982 | Colvocoresses | 356/2 |
| 4,390,785 | 6/1983 | Faulhaber et al. | 250/330 |
| 4,902,893 | 2/1990 | Burrer | 250/334 |
| 5,028,138 | 7/1991 | Wolff | 356/369 |
| 5,093,563 | 3/1993 | Small et al. | 250/201.9 |
| 5,149,959 | 9/1992 | Collins et al. | 250/226 |
| 5,166,755 | 11/1992 | Gat | 356/419 |
| 5,187,754 | 2/1993 | Currin et al. | 382/54 |
| 5,270,528 | 12/1993 | Ogikubo | 250/201.7 |
| 5,276,321 | 1/1994 | Chang et al. | 250/226 |

*Primary Examiner*—John B. Sotomayor

[57] ABSTRACT

A focal plane imaging array (FPIA) (16) for use in a direct detection imaging device (10) for conducting radiometric imaging at microwave and millimeter-wave frequencies is disclosed as having an internal electronic calibration source (36). The plurality of energy detecting pixel elements (14) which comprise the FPIA (16) include a detection circuit (34) and a calibration circuit (36). The calibration circuit (36) is uni-directionally coupled to the detection circuit (34) to allow a known calibration signal "pulse" to be introduced into the detection circuit (34). The calibration pulse is processed by the pixel detection circuit and the output signal is compared with the pixel's responsivity value. Adjustments in the pixel gain and sensitivity may then be made as appropriate.

16 Claims, 1 Drawing Sheet

FOCAL PLANE IMAGING ARRAY WITH INTERNAL CALIBRATION SOURCE

BACKGROUND OF THE INVENTION

1. Technical Field

The present invention relates generally to imaging devices having focal plane imaging arrays and, more particularly, to a focal plane imaging array for a direct detection imaging device capable of conducting radiometric imaging at microwave or millimeter-wave frequencies.

2. Discussion

Direct detection radiometric imaging is an imaging technique that involves scanning a field of view and collecting the radiant electromagnetic energy which is reflected and/or emitted by unknown objects and converting that energy into useful image data. Direct detection imaging, which is a passive imaging technique, differs from active imaging methods, such as radar imaging, which generates pulses of radiation that are first transmitted outward toward the field of view and then received as they are reflected back by the objects in the field of view. Typically, direct detection imaging devices employ an optical system to collect the radiant electromagnetic energy emanating from the objects in the field of view, a focal plane imaging array (FPIA) to detect the energy and produce an output, additional electronics, such as an interface unit and processing unit, which converts the output of the FPIA into useable image data and, finally, an output display unit for displaying a resultant visible image.

An FPIA is generally comprised of an array of energy detecting pixel elements which are positioned at the focal plane of the optical system of the imaging device. As the imaging device scans a field of view, the energy is received and detected at each pixel of the FPIA.

Direct detection radiometric imaging at microwave or millimeter-wave frequencies possesses unique advantages which are desirable in a variety of military, scientific and commercial imaging applications, including surveillance systems, mapping and navigation systems. In particular, at these frequencies, which are relatively low in the realm of direct detection radiometric imaging, low visibility obstacles do not inhibit the ability to perform the imaging function and obtain useable image data. For example, the thermal radiation that is emitted at microwave or millimeter-wave frequencies by objects is capable of penetrating atmospheric conditions such as fog, haze, light rain, dust and smoke. Consequently, radiometric imaging at these frequencies is not impeded by such phenomena.

However, because radiant electromagnetic energy emissions at microwave or millimeter-wave frequencies are generally very weak, the FPIAs used in direct detection radiometric imaging devices for these frequencies must be extremely sensitive. Further, as these imaging devices process the received energy, they must not significantly distort the level of energy that is detected. That is, they must have extremely low inherent noise characteristics.

Presently, direct detection imaging devices performing imaging at microwave or millimeter-wave frequencies employ FPIAs that are very expensive because they are based upon labor intensive, microwave integrated circuit (MIC) technology. In addition, due in part to the costly MIC manufacturing techniques, only a few hundred pixels can be economically integrated into an FPIA, where thousands of pixels are desirables. This results in a FPIA with a severely limited field of view. Consequently, present FPIAs used for direct detection radiometric imaging at microwave or millimeter-wave frequencies are prohibitively costly to all but a limited number of users.

Further, present FPIAs offer a limited imaging throughput capability because they employ a slow, mechanical calibration source for system gain adjustments, a critical task which must be performed frequently to minimize systematic errors in the FPIA pixels due to gain drifts. Presently, calibration of the FPIA pixels by mechanical means may take anywhere from several seconds to several minutes. Still further, the mechanical calibration source adds significantly to the size and weight of the imaging device.

In light of the above discussion, it has been considered very desirable to develop new FPIA designs for use in direct detection microwave or millimeter-wave radiometric imaging devices which overcome the above disadvantages associated with the current technology.

SUMMARY OF THE INVENTION

In accordance with the teachings of the present invention, a focal plane imaging array (FPIA) for use in a direct detection imaging device for conducting radiometric imaging at microwave and millimeter-wave frequencies is disclosed as having an internal electronic calibration source. The plurality of energy detecting pixel elements which comprise the FPIA include a detection circuit and a calibration circuit. The calibration circuit is uni-directionally coupled to the detection circuit to allow a known calibration signal "pulse" to be introduced into the detection circuit from the calibration circuit. The calibration pulse is processed by the pixel detection circuit. The pixel output signal is then compared with the pixel's responsivity value. Adjustments in the pixel gain and sensitivity may then be made as appropriate.

The present invention is expected to exhibit the advantages of improved accuracy and higher imaging throughput over conventional FPIAs because of the internal electronic calibration source, which enables a multi-level system gain calibration to be accomplished in a time span on the order of milliseconds. In addition, because the calibration source, has no mechanical or moving parts, the present invention can be more compact, efficient, and reliable than conventional microwave and millimeter-wave FPIAs. Further, the pixel of the MMIC FPIA simplifies the design and assembly of the FPIA and the components of the present invention can be fabricated at a low cost on a single chip with InGaAs HEMT MMIC technology.

BRIEF DESCRIPTION OF THE DRAWINGS

The various advantages of the present invention will become apparent to one skilled in the art upon reading the following specification, in which.

DESCRIPTION OF THE PREFERRED EMBODIMENT

Figure 1:
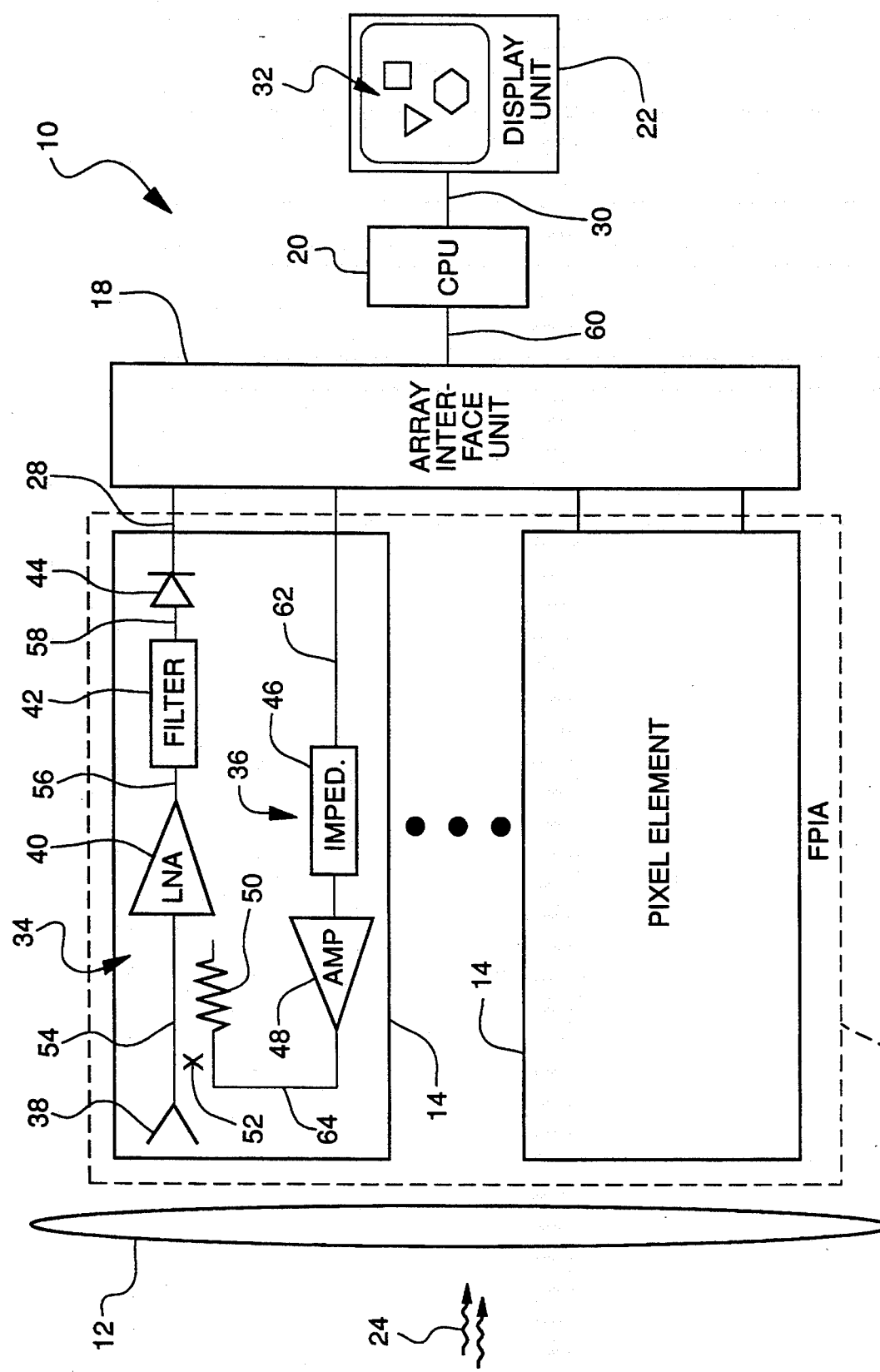
FIG. 1 is a simplified block diagram illustrating a direct detection imaging device for conducting radiometric imaging at millimeter-wave frequencies incorporating the focal plane imaging array with an internal electronic calibration source of the present invention.

It should be understood from the outset that while the following discussion illustrates a particular embodiment of the present invention, this embodiment merely represents a best mode of currently practicing the invention and other modifications may be made to the particular embodiment without departing from the spirit and scope of the invention.

Referring now to the drawing, a simplified block diagram of a direct detection imaging device for conducting radiometric imaging at millimeter-wave frequencies and incorporating the focal plane imaging array (FPIA) with an internal electronic calibration source of the present invention is illustrated in FIG. 1. As previously described and shown in the drawing, the direct detection imaging device 10 includes an optical system 12, a plurality of energy detecting pixel elements 14 arranged in an imaging array located at the focal plane of the optical system 12, or FPIA 16, processing electronics including an array interface unit 18 and a central processing unit (CPU) 20, and an output display unit 22.

Imaging is initiated as the imaging device 10 surveys a field of view for radiant electromagnetic energy 24 that is emitted and/or reflected at microwave or millimeter-wave frequencies by unknown objects 26 in that field of view. As the imaging device 10 scans the field of view, the radiant energy 24 is collected by the optical system 12 and focused on the pixels 14 in the FPIA 16 where it is received. Each pixel 16, in turn, processes the received signal 24 and generates an analog output signal 28 that corresponds to the level of energy 24 that the pixel receives. The array interface unit 18 coordinates communicating the output signal 28 of each pixel 14 to the CPU 20. At the CPU 20, image data 30 is generated from the output 28 of the FPIA 16. Finally, the image data 30 is displayed as a visible image 32 on the output display unit 22.

As illustrated in FIG. 3, each pixel 14 in the focal plane imaging array 16 includes a detection circuit 34 and a calibration circuit 36. The detection circuit 34 includes a receiving antenna 38, a low noise amplifier (LNA) 40, a band pass filter 42, and a video detector 44. The calibration circuit 36 includes a source impedance 46, a calibration amplifier 48 and a resistance 50. Further, the calibration circuit 36 is uni-directionally coupled to the detection circuit 34 by a directional coupler 52.

In the pixel detection circuit 34, the receiving antenna 38 receives the radiant energy 24 which has been collected by the optical system 12. The signal 54 is then carried to the LNA 40 where it is amplified. Next, the amplified signal 56 is filtered at filter 42. Filtered signal 58 is subsequently passed to the video detector 44 where the received power is detected and an analog output signal 28, such as a voltage or current, is generated.

Because the radiant energy 24 emitted and/or reflected at microwave and millimeter-wave frequencies by objects 26 is typically very weak, a direct detection imaging device 10 for radiometric imaging at these frequencies must incorporate an extremely sensitive receiving antenna 38. In particular, the receiving antenna 38 can be a Vivaldi antenna which is optimized for receiving signals having frequencies ranging from 10–100 GHz.

Also due to the characteristically weak signal, it is critical that no significant amount of noise or other distortion is injected or introduced into the pixel detection circuit 34 during signal processing. Consequently, it is important that the LNA 40 exhibit high gain yet have a low noise figure, such as a LNA providing signal gain on the order of 40–60 dB while having a noise figure ranging from 0.5–5.5 dB over a frequency range of 10–100 GHz. One such commercially available LNA is sold by TRW under the part number designation AET101C, which is a seven stage, 40 dB amplifier having a noise figure of 5.5 dB over a frequency range of 90 to 95 GHz and is produced on a 2.7 mm $\times$ 3.5 mm InGaAs HEMT MMIC chip.

From the LNA 40, the amplified signal 56 is passed to the bandpass filter 42, where the signal is narrowed toward two regions of the received frequency band. It has been determined that 37 GHz $\pm$ 5 GHz and 94 GHz $\pm$ 5 GHz are preferable because of windows in the atmospheric attenuation.

The filtered signal 58 next proceeds to the video detector 44 where the received power is detected. The video detector 44 is a suitable video diode detector having a wide band width, such as a beam-lead Schottky-diode detector with a responsivity of 7.2 V/mW and a tangential sensitivity of $-43$ dBm at 94 GHz. The video detector 44 generates an analog output signal, such as a voltage, that corresponds to the power detected.

The output signal 28 is then carried to the array interface unit 18. The array interface unit 18 serves a multiplexer for controlling the communication between the CPU 20 and the plurality of pixels 14 in the FPIA 16 in a well-known manner. At the array interface unit 18, the analog output signal 28 is conditioned for use by the CPU 20, such as by an analog-to-digital conversion. A serial data stream 60 is then passed from the array interface unit 18 to the CPU 20 for image processing and enhancement. From the CPU 20, useable image data 30 is carried to the output display unit 22 where a resultant visible image 32 is displayed.

As already discussed, each pixel 14 in the FPIA 16 of the present invention includes an electronic calibration circuit 36. The calibration circuit 36 allows the pixel gain calibration to be performed quickly and frequently to prevent systematic errors in the FPIA pixels 14 due to unwanted gain drifts. In order to calibrate the FPIA 16, the responsivity of each FPIA pixel 14 must first be determined. Each pixel 14 in the FPIA 16 is exposed to both "hot" and "cold" loads of known temperatures, for example room temperature and the temperature of liquid nitrogen, respectively. The output voltage 28 of each pixel 14 is measured under each load. The pixel's responsivity is then determined by dividing the difference between the output voltages measured under each load by the difference between the temperatures of the loads. Pixel responsivity is measured in units of mV/°K.

After the responsivity of each pixel 14 in the FPIA 16 is initially identified, calibration of the FPIA 16 is possible by introducing a known pulse of energy into each pixel's detection circuit 34 to verify the accuracy of the output voltage generated 28 by that pixel 14 in accordance with the pixel's 14 responsivity. Recalibration of the FPIA pixels 14 is initiated by the CPU 20 and takes place when the imaging function is disabled. A calibration signal 62 is originated by the CPU 20 and passed to a pixel 14 by the array interface unit 18. Noise power, which is generated by the source impedance 46, adds to the calibration signal 62. The calibration signal 62 is then amplified at the calibration amplifier 48. A very small known pulse of energy from the amplified calibration signal 64 is then coupled to the detection circuit 34 by the directional coupler 52, which is adjustable to control the level of the calibration signal 64 that is coupled from the calibration circuit 36 to the detection circuit 34. This known pulse of energy is on the order of magnitude of the energy that is received by the receiving antenna 38 while the imaging device 10 is performing the imaging function. The remainder of signal 64 is dissipated in resister 50. The pulse is then processed in the pixel detection circuit 34 as already described. The pixel output signal 28 is then measured and verified against that pixel's 14 responsivity value. Adjustments to the LNA 40 gain and/or video diode 44 sensitivity to correct the pixel output signal 28 can then be made, if necessary.

Electronic calibration of each FPIA pixel 14 can be accomplished in a time span on the order of milliseconds, as compared to the several seconds to a few minutes it may take with conventional mechanical calibration means. Calibration may be repeated as often as necessary.

The circuit elements of the FPIA pixel 14 can be incorporated into a single monolithic microwave integrated circuit (MMIC) semiconductor chip utilizing InGaAs HEMT MMIC technology. Thus, the FPIA pixel 14 can be fabricated in high volume at a low cost.

The FPIA 16 of the present invention is more compact, efficient and reliable than conventional microwave or millimeter-wave FPIAs and offers the advantages of having no mechanical moving parts, greater accuracy and higher data throughput. Also, fast internal multi-level system gain calibration is achievable through an electronic calibration circuit 36 that is integrated into the FPIA pixel 14. The present invention may be used in a variety of applications including ground-based, airborne, and space borne microwave and millimeter-wave radiometry and radiometric imaging.

Various other advantages and modifications will become apparent to one skilled in the art after having the benefit of studying the teachings of the specification, the drawings, and the following claims.

What is claimed is:

1. An energy detecting pixel element for use in a focal plane imaging array for a direct detection imaging device, said pixel element comprising a detection circuit for receiving and detecting radiant electromagnetic energy at microwave and millimeter-wave frequencies, a calibration circuit for calibrating said pixel element, said calibration circuit being electronically coupled to said detection circuit by a directional coupler, said directional coupler being operable to enable a known portion of a calibration signal to be introduced into said detection circuit from said calibration circuit, and wherein said detection circuit, said calibration circuit and said directional coupler are monolithically integrated onto a single computer chip.

2. The pixel element of claim 1 wherein said detection circuit comprises receiving antenna means, first amplification means, bandwidth filter means and video detection means and said calibration circuit comprises impedance means, second amplification means and resistance means.

3. The pixel element of claim 2 wherein said receiving antenna means is optimized for receiving signals at frequencies ranging from 10 to 100 GHz.

4. The pixel element of claim 3 wherein said receiving antenna means is a Vivaldi antenna.

5. The pixel element of claim 2 wherein said first amplification means is capable of providing signal gain on the order of about 40 to 60 dB while having a noise figure ranging from about 0.5 dB to 5.5 dB over a frequency range of about 10 to 100 GHz.

6. The pixel element of claim 2 wherein said video detection means has a responsivity of about 7.2 V/mW and a tangential sensitivity of about −43 dBm at a frequency of about 94 GHz.

7. The pixel element of claim 6 wherein said video detection means is a beam-lead Schottky diode.

8. A focal plane imaging array for use in a direct detection imaging device for conducting radiometric imaging at microwave and millimeter-wave frequencies, comprising:

a plurality of energy detecting pixel elements for receiving and detecting radiant electromagnetic energy at microwave or millimeter-wave frequencies and generating an output signal, each said pixel element including a detection circuit for detecting said radiant electromagnetic energy, a calibration circuit for calibrating said output signal of each said pixel, and a directional coupler, said directional coupler being operable to enable a know portion of a calibration signal to be introduced into said detection circuit from said calibration circuit, and wherein said detection circuit, said calibration circuit and said directional coupler are monolithically integrated onto a single computer chip.

9. The focal plane imaging array of claim 8 wherein said detection circuit comprises receiving antenna means, first amplification means, bandwidth filter means and video detection means and said calibration circuit comprises impedance means, second amplification means and resistance means, and said directional coupler is a uni-directional coupler.

10. The focal plane imaging array of claim 9 wherein said receiving antenna means is optimized for receiving signals at frequencies ranging from 10 to 100 GHz.

11. The focal plane imaging array of claim 10 wherein said receiving antenna means is a Vivaldi antenna.

12. The focal plane imaging array of claim 9 wherein said first amplification means is capable of providing signal gain on the order of about 40 to 60 dB while having a noise figure ranging from about 0.5 dB to 5.5 dB over a frequency range of about 10 to 100 GHz.

13. The focal plane imaging array of claim 9 wherein said video detection means has a responsivity of about 7.2 V/mW and a tangential sensitivity of about −43 dBm at a frequency of about 94 GHz.

14. The focal plane imaging array of claim 13 wherein said video detection means is a beam-lead Schottky diode.

15. A direct detection imaging device for conducting radiometric imaging at microwave and millimeter-wave frequencies, comprising:

an optical system for collecting radiant electromagnetic energy emitted or reflected at microwave or millimeter-wave frequencies by unknown objects in a field of view;

a focal plane imaging array comprising a plurality of energy detecting pixel elements for receiving and detecting said radiant electromagnetic energy and generating an output signal;

processing electronics for communicating with said pixel elements of said focal plane array, generating a calibration signal for calibrating said pixel elements and processing said output signal and generating image data; and an output display unit for displaying a resultant visible image; wherein each said pixel element is comprising a detection circuit and a calibration circuit, said calibration circuit being electronically coupled to said detection circuit by a directional coupler, said directional coupler being operable to enable a known portion of said calibration signal to be introduced into said detection circuit from said calibration circuit, and wherein said detection circuit, said calibration circuit and said directional coupler are monolithically integrated onto a single computer chip.

16. An energy detecting pixel element for use in a focal plane imaging array for a direct detection imaging device, said pixel element comprising detection means for receiving and detecting radiant electromagnetic energy at microwave and millimeter-wave frequencies and electronic calibration means for calibrating said pixel element, said calibration means including coupling means for electronically coupling said calibration means to said detection means to enable a known portion of a calibration signal to be introduced into said detection means from said calibration means, and wherein said detection means and said calibration means are monolithically integrated onto a single computer chip.

* * * * *